United States Patent [19]

Byers et al.

[11] Patent Number: 4,686,765
[45] Date of Patent: Aug. 18, 1987

[54] METHOD FOR MAKING AN INTRACOCHLEAR ELECTRODE ARRAY

[75] Inventors: Charles L. Byers, Vacaville, Calif.; Gerald E. Loeb, Clarksburg, Md.; Michael M. Merzenich; Stephen J. Rebscher, both of San Francisco, Calif.

[73] Assignee: Regents of the University of California, Berkeley, Calif.

[21] Appl. No.: 855,084

[22] Filed: Apr. 22, 1986

Related U.S. Application Data

[62] Division of Ser. No. 607,019, May 3, 1984, abandoned.

[51] Int. Cl.<sup>4</sup> ............................................. H01R 43/00
[52] U.S. Cl. .................................. 29/858; 264/272.15; 264/272.16; 128/420.6; 128/784
[58] Field of Search .................... 29/858; 179/107 FD, 179/107 E; 264/272.14, 272.15, 272.16, 277

[56] References Cited

U.S. PATENT DOCUMENTS 4,284,856 8/1981 Hochmair et al. .............. 179/107 E
4,400,590 8/1983 Michelson ..................... 179/107 FD

OTHER PUBLICATIONS

"Multichannel Cochlear Implants: Electrode Design Surgical Considerations", pp. 258–260; R. A. Schindler et al., *Artificial Organs*, 1981.
"Cochlear Implants: Case Selection and Technique", pp. 55–62; B. F. O'Reilly, Ear, Nose & Throat Journal, 1981.
"Design and Fabrication of an Experimental Cochlear Prosthesis"—pp. 241–254, G. E. Loeb et al, Medical & Biological Engineering and Computing, distributed 1983.

*Primary Examiner*—Howard N. Goldberg
*Assistant Examiner*—Carl J. Arbes
*Attorney, Agent, or Firm*—Phillips, Moore, Lempio & Finley

[57] ABSTRACT

A method is disclosed for making an intracochlear multielectrode array having a spiral configuration, at least generally conforming to the scala tympani of a cochlea. The array is formed in a two-part mold and comprises an elastomeric carrier supporting a plurality of metallic electrodes in fixed positions thereon. Each electrode has an associated lead to provide a plurality of leads and composite rib structure extending from a basal portion of the array to an apical portion thereof. Each electrode and associated lead is formed from a flattened metallic wire. The wire leads are stacked in the mold to permit the wires to flex in the direction of their spiral curvatures, facilitating insertion of the array into a cochlear, but to prevent transverse flexing thereof.

19 Claims, 18 Drawing Figures

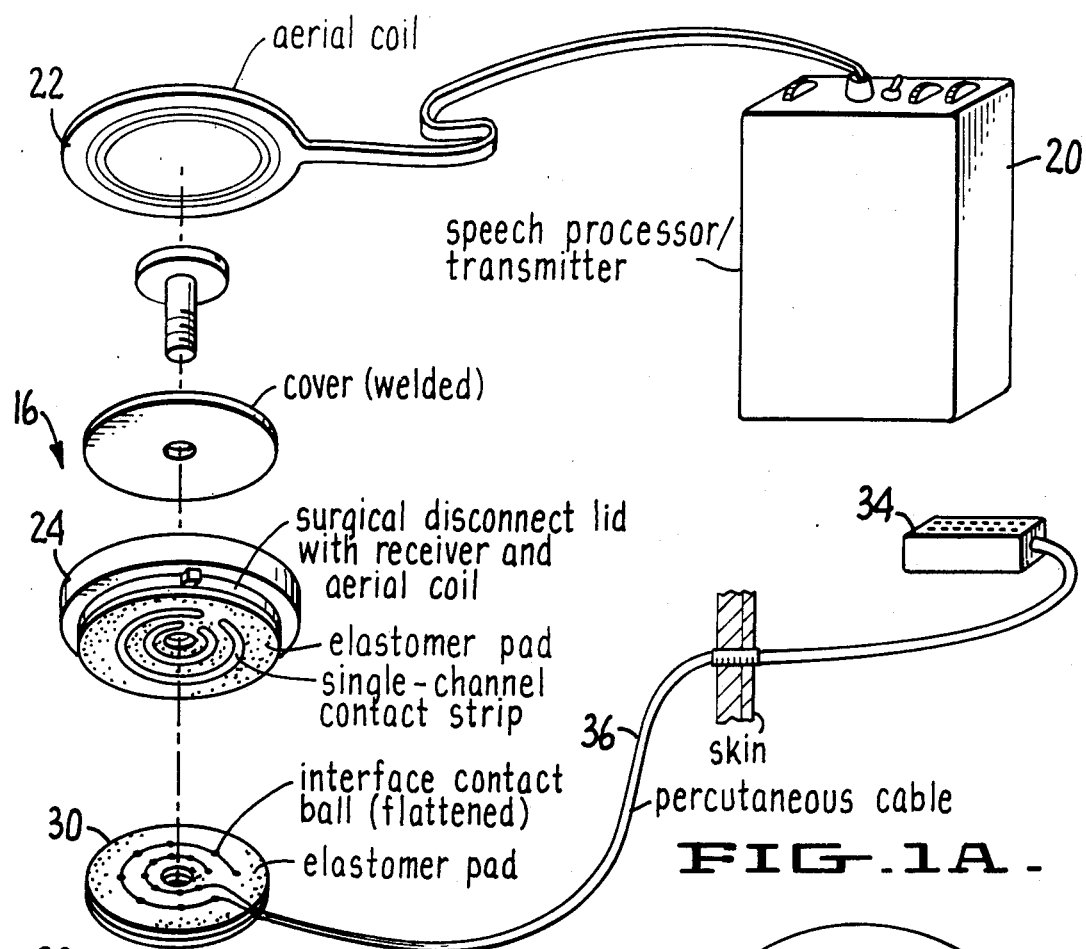
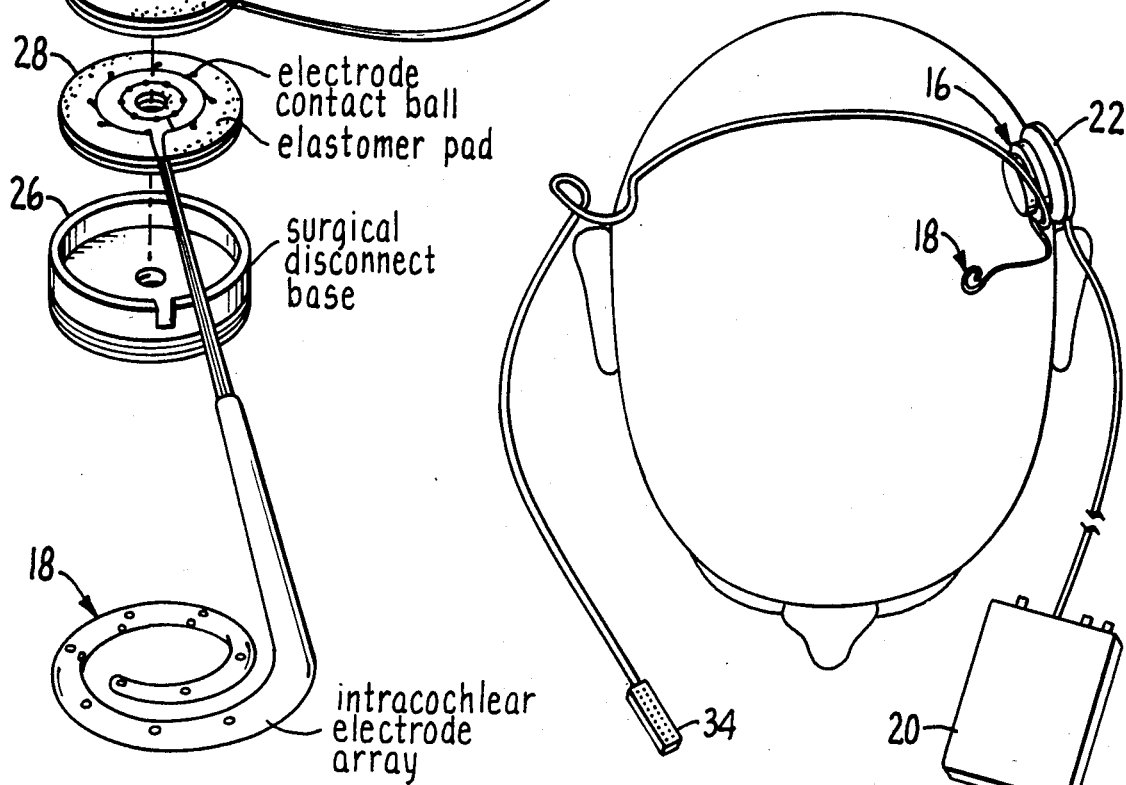
FIG.1A.
FIG.1B.

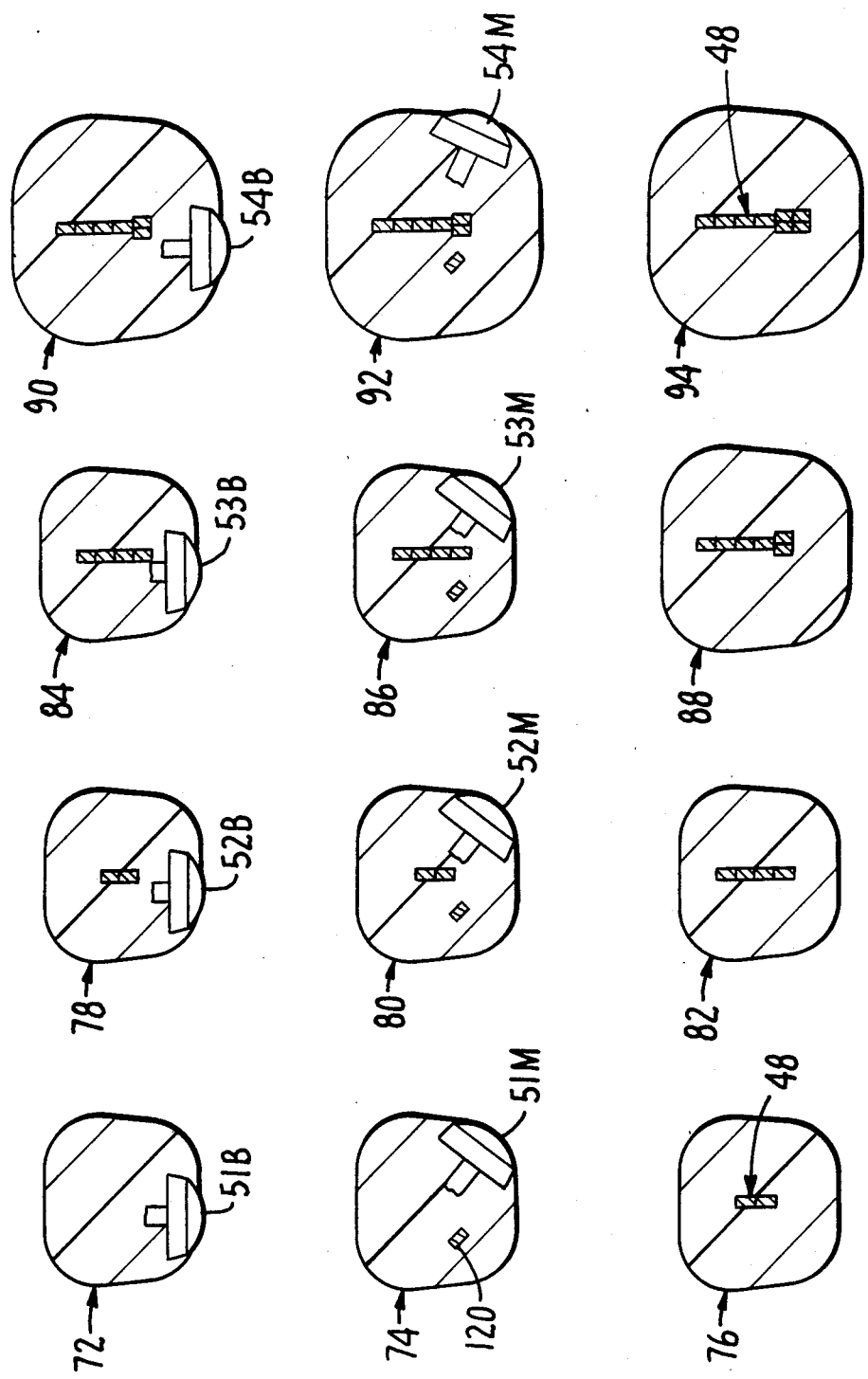

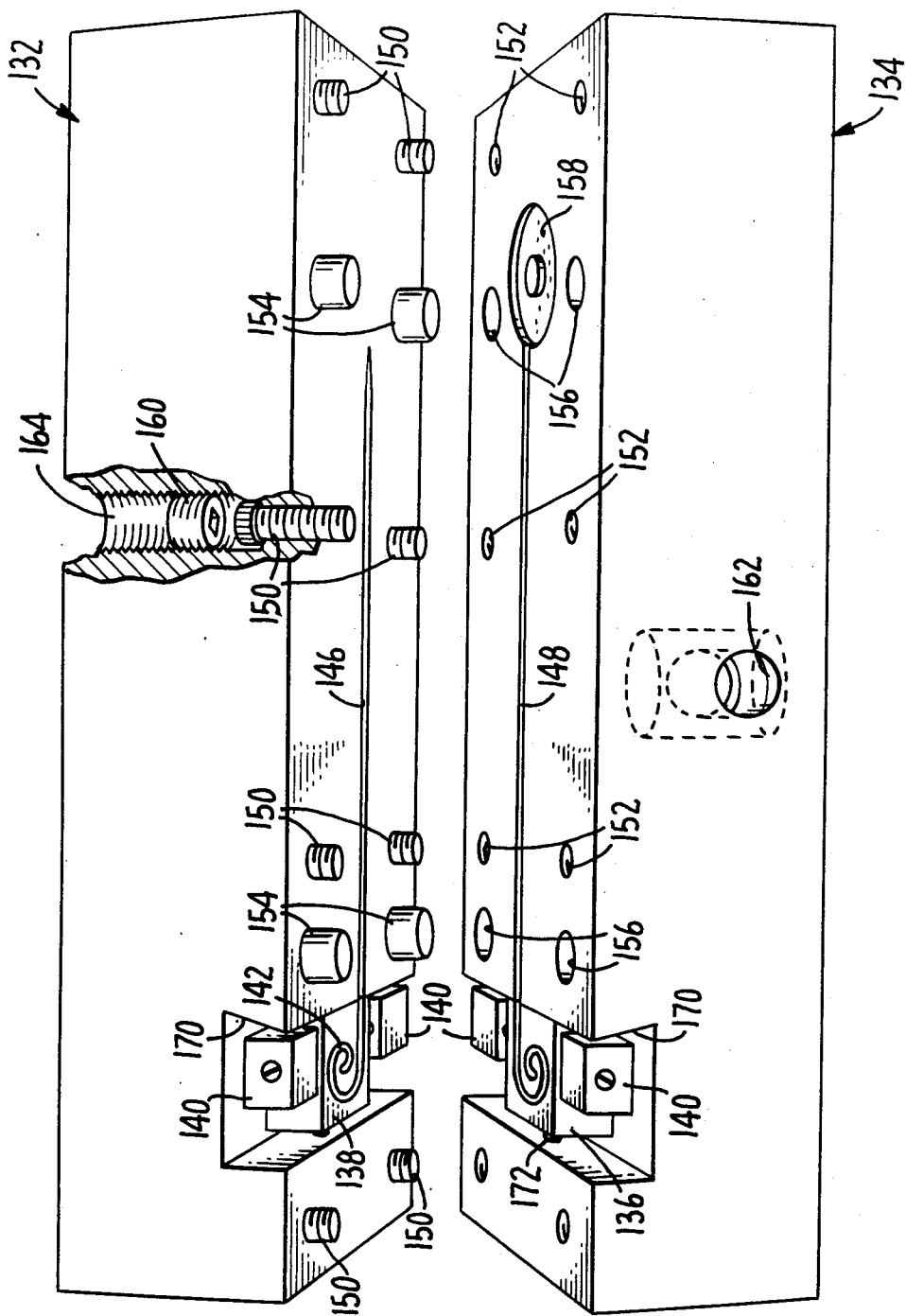

4,686,765

METHOD FOR MAKING AN INTRACOCHLEAR ELECTRODE ARRAY

BACKGROUND OF THE INVENTION

This invention was made with Government support under Contract No. N01-NS-0-2337 awarded by the Department of Health and Human Services. The Government has certain rights in this invention.

This is a division of Ser. No. 607,019, filed May 3, 1984, now abandoned.

FIELD OF THE INVENTION

The present invention relates generally to hearing prostheses and more specifically to an electrode array for implanting in the cochlea of an ear.

BACKGROUND ART

Cochlear prosthesis devices are currently being developed to restore hearing in the profoundly deaf. Such prostheses utilize an electrode array which is inserted in the scala tympani of the cochlea and is used to stimulate the auditory nerves. Exemplary arrays are described and referred to in various publications including R.A. Schindler, et al., "Multichannel Cochlear Implants: Electrode Design Surgical Considerations," Proceedings of the Third Meeting of ISAO printed in *Artificial Organs* (Suppl.), pp. 258–260, 1981 and M.M. Merzenich, et al., "Cochlear Implant Prostheses: Strategies and Progress," *Annals of Biomedical Engineering*, Vol. 8, pp. 361–368, 1980.

The subject electrode array is superior to the electrode arrays of the type disclosed or referred to in the above-referenced publications and is capable of providing improved performance under safer operating conditions. In addition, the array can be implanted in the cochlea with reduced likelihood of injury.

BRIEF DESCRIPTION OF THE DRAWINGS

FIG. 1A is an exploded view of an exemplary intracochlear electrical stimulation system utilizing the subject electrode array.

FIG. 1B is an illustration generally depicting the manner in which the FIG. 1A system is positioned in a patient.

FIGS. 6A and 6B are schematic cross-sectional views of the preferred embodiment electrode array of FIG. 3 and FIG. 6c is a cross-sectional view of one portion of the central rib structure of the array.

FIG. 7 is an elevational view of a casting fixture used in the fabrication of the subject electrode array.

SUMMARY OF THE DISCLOSURE

Figure 3:
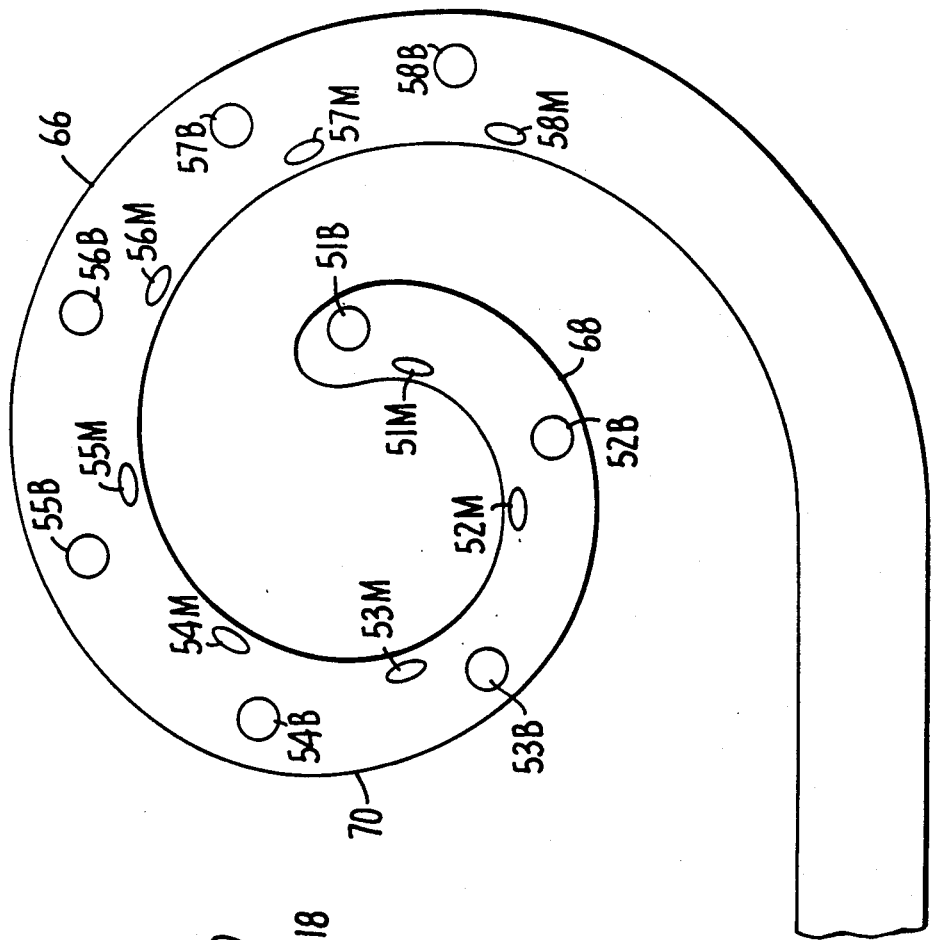
FIG. 3 is a plan view of a preferred embodiment of the subject electrode array.

An electrode array is disclosed for implantation in a human cochlea. The array includes a spiral-shaped resilient carrier and a plurality of electrodes, with each electrode including an associated electrode lead. The electrodes are supported in the carrier, with the leads extending down the center of said carrier so as to form a central rib structure. The leads have an elongated cross-section and are individually vertically aligned in the rib structure so as to limit flexing of the array in a vertical direction.

DETAILED DESCRIPTION OF THE PREFERRED EMBODIMENT OF THE INVENTION

Referring now to the drawings, the FIG. 1A system utilizes an implanted assembly which includes a surgical disconnect/receiver, generally designated by the numeral 16, coupled to an intracochlear electrode array, generally designated by the numeral 18. The external components of the system include a speech processor/transmitter 20 which drives an antenna coil 22. The electrode array is of the general type referred to in Loeb, G.E., et al., "Design and Fabrication of an Experimental Cochlear Prosthesis" *Medical and Biological Engineering and Computing*, Vol. 21, pp. 241–254, 1983 and Merzenich, M. M., et al., "The UCSF Cochlear Implant Project" *Advances in Audiology*, Vo. 2, pp. 119–144 (1984) the contents of which are both hereby fully incorporated herein by reference.

Surgical disconnect/receiver 16 comprises a lid 24 which contains the passive radio receiver and associated antenna coil. Lid 24 also includes an elastomer pad with a pair of electrical contact strips coupled to the output of the receiver. Receiver 16 further includes a base 26 and a pair of elastomer contact pads 28 and 30 intermediate the base and lid 24. Elastomer contact pad 28 is connected to electrode array 18 and contact pad 30 is connected to a percutaneous cable 36 which is, in turn, connected to an external connector 34.

When lid 24 is secured to base 26 with contact pads 28 and 30 disposed there between, the output of the receiver is electrically connected through the pad to electrode array 18. In addition, external connector 34 is connected to the array and receiver output. Connector 34 may be used either to monitor the output of the receiver or to stimulate the electrode array.

Speech processor/transmitter 20 includes a pocket-size sound processor and transmitter box contains conventional components of a high quality hearing aid (microphone, batteries, thresh hold and volume control) plus an R.F. generator and internally adjustable compressors and filters which are set during clinical testing to optimize speech intelligibility.

Referring now to FIG. 1B, the surgical disconnect/receiver 16 is mounted behind the ear of the patient with the receiver coil being affixed to the mastoid bone.

As will be subsequently described in greater detail, the spiral-shaped intracochlear section of electrode array 18 is implanted in the scala tympani of the cochlea and is coupled to surgical disconnect/receiver 16 by way of the elongated lead section of the array. The surgical implant procedure involves exposure of the mastoid cortex and external auditory canal of the implanted ear via elevation of a postauricular skin flap. A shallow (2 mm deep) circular depression is drilled into the mastoid cortex using a specially designed trephine. Disconnect/receiver 16 will later be seated in this depression. A continuous narrow, shallow undercut grove is cut into the boney ear canal and over the mastoid from the disconnect/receiver site into the middle ear cavity. The round window of the cochlea is exposed and removed. The window is then enlarged by about 3 mm to provide an unrestricted view of the first turn of the scala tympani. The electrode is then carefully inserted into the opening. Antenna coil 22 will be positioned on the skin directly over the receiver coil when the incision has healed.

Percutaneous cable 13 is intended for monitoring and testing and may be removed by a simple surgical procedure wherein lid 24 is disconnected from base 26. Percutaneous cable 36 is severed and contact pad 30 is removed. Finally, cable 36 is pulled through the opening in the skin, and the lid, and base are reconnected, thereby coupling the output of the receiver directly to electrode array contact pad 28. 20 It should be further noted that the receiver can be easily replaced in the event of failure or the like in a similar manner without removing electrode array 18 from the cochlea.

Although electrode array 18 is depicted in a single channel system, the array is also suitable in multiple channel applications. An exemplary multichannel application is disclosed in U.S. Pat. No. 4,400,590, the contents of which are fully incorporated herein by reference.

Figure 2:
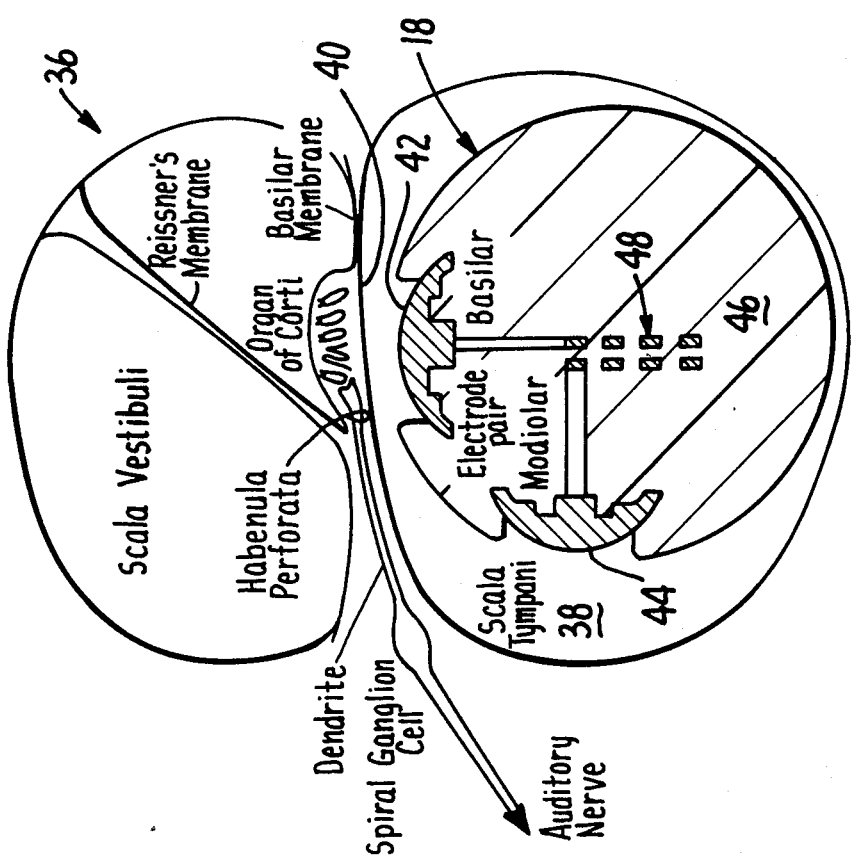
FIG. 2 is a cross-section schematic representation of the cochlea with an exemplary electrode array implanted in the scala tympani.

The intracochlea section of electrode array 18 has a spiral shape which generally corresponds to the shape of the scala tympani of the cochlea as shown in FIG. 2. The array should loosely fit the dimensions of the scala, and should bring the basilar electrodes into very close proximity with the basilar membrane without applying any pressure to this extremely delicate structure. As will be subsequently described, array 18 should be also sufficiently small to permit the perilymph in the cochlea to freely circulate.

Array 18 preferably includes eight electrode pairs spaced along the length of the cochlear section although a fewer or greater number of pairs may be used. The pairs are imbedded in a resilient elastomer carrier, molded to fit the Scala Tympani. An elastomer sold by Dow Corning under the trademark Silastic MDX44210 has been found to be suitable for the present application. Referring now to FIG. 2, each electrode pair includes a basilar electrode 42, which is positioned facing the basilar membrane and a modiolar electrode 44, which is positioned facing the modiolus (through which the auditory nerve extends) at the center of the cochlear spiral. In the embodiment depicted in FIG. 2, the basilar and modiolar electrodes are positioned at right angles with respect to another. Although both electrodes are visible in FIG. 2, it is preferred that the electrodes of each pair be longitudinally displaced from one another. As will be subsequently described, each electrode has an integral lead which generally extends down the central portion of carrier towards the lead section of the array. The grouped leads form a central rib structure, generally designated by the numeral 48, which controls flexing of the array in a predetermined manner.

Referring now to FIG. 3, the intracochlear section of a preferred embodiment electrode array may be seen. This particular embodiment preferably includes eight pairs of electrodes, with six pairs being the minimum number required to achieve the full benefit of the subject invention. The eight basilar electrodes 51B through 58B extend generally along the upper surface of the array so as to face the basilar membrane (FIG. 2). When implanted in the cochlea, the eight modiolar electrodes 51M through 58M extend generally along the inner periphery of the spiral and face the modiolus when implanted.

Preliminary studies have indicated that the dimensions of the scala tympani do not vary greatly from individual to individual, including children and adults. The FIG. 4 graph shows the distance from basilar membrane to floor of the scala tympani versus the distance from the round window taken from Woods metal castings from four adult temporal bones. The scala tympani depicted by curves 64 and 65 are believed to be of normal dimensions with curves 60 and 62 being somewhat unusually large and small, respectively.

In order to provide optimum performance, it is desirable for the intracochlear array to extend approximately 24 mm into the scala tympani from the round window. In order to achieve the desired degree of insertion, the intracochlear section of the subject electrode array is provided with a relatively large diameter basal portion 66, a relatively small diameter apical portion 68 and a tapered portion 70 intermediate the basal and apical portions.

Figure 4:
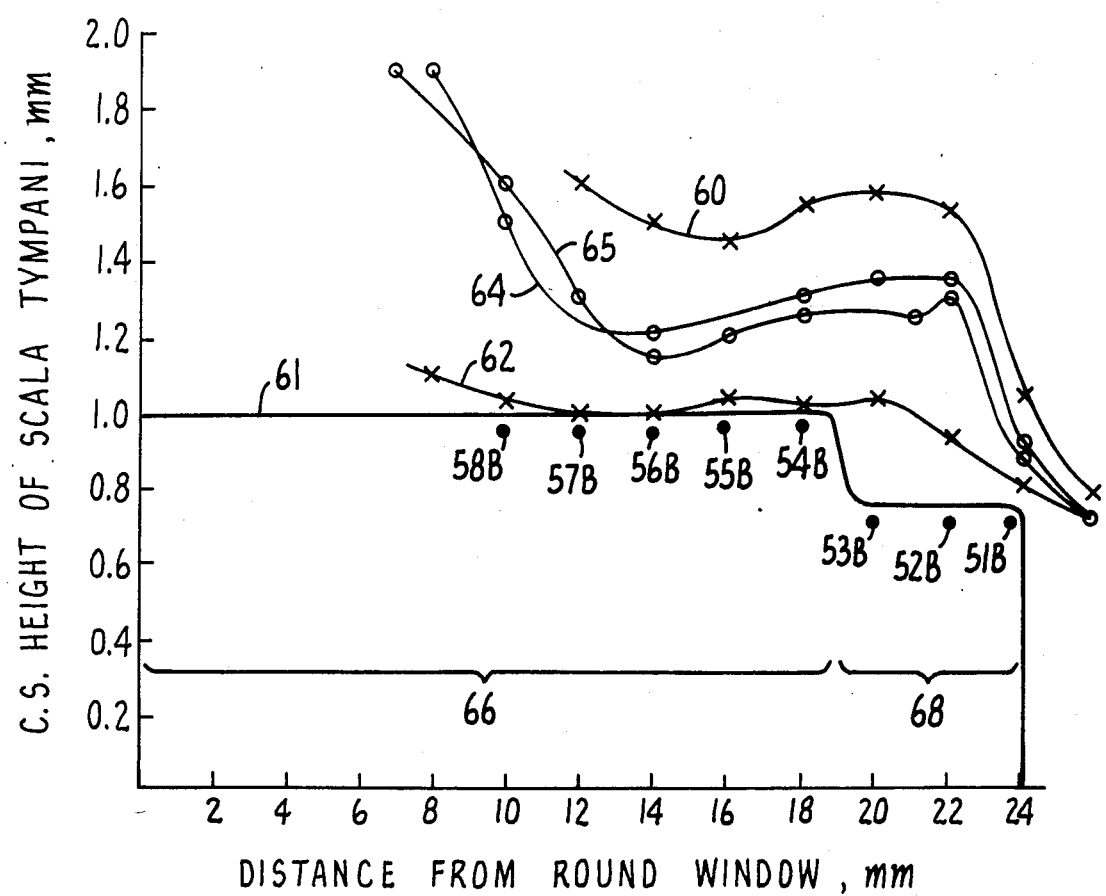
FIG. 4 is a graph illustrating the dimensions of the preferred embodiment of the subject electrode array with respect to the typical range of height dimensions for the human scala tympani.

FIG. 4 further includes a curve 61 which represents the diameter of the intracochlea section of the subject array as measured from the round window when the array has been implanted. The position of the basilar electrodes 51B through 58B in the array are also schematically depicted (the modiolar electrodes are not shown). As can be seen from curve 61, the basal portion 66 of the array will preferably extend into the scala tympani approximately 18 mm, with the taper portion 70 being positioned at approximately 18-20 mm. The apical portion 68 of the array typically extends from approximately 20 mm to 24 mm.

As can be seen from curves 60, 62, 64 and 65, the scala tympani has a constriction located at approximately 14 to 16 mm from the round window. This constriction limits the maximum diameter of the basal portion 66 of the array. Similarly, the cross-sectional area of the scala tympani begins to diminish substantially in the apex region of the cochlea at approximately 20 mm. The reduced cross-sectional area of the apical portion 68 of the array is provided to accommodate the reduced cochlear volume in this area and permit free circulation of the perilymph contained in the scala tympani.

The preferred embodiment electrode array is provided with a basal portion 66 having a diameter of approximately 1mm and an apical portion 68 having a diameter of approximately 0.75 mm. These dimension are believed to be suitable for most patients. A somewhat smaller diameter electrode array would be appropriate for a patient having a scala tympani as represented by curve 62 since the preferred embodiment array would actually contact the basilar membrane, this being undesirable.

Figure 5:
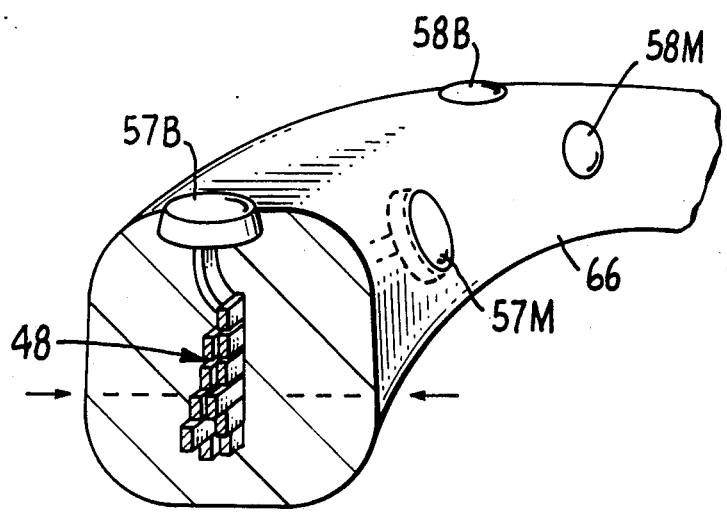
FIG. 5 is a cross-sectional elevation view of the preferred embod,iment electrode array.

FIG. 5 shows an exemplary cross-sectional view of the preferred embodiment electrode array taken through a section located at basilar electrode 57B. All electrodes include integral insulated leads which extend through the central portion of the carrier to form central rib structure 48.

Figure 6B:
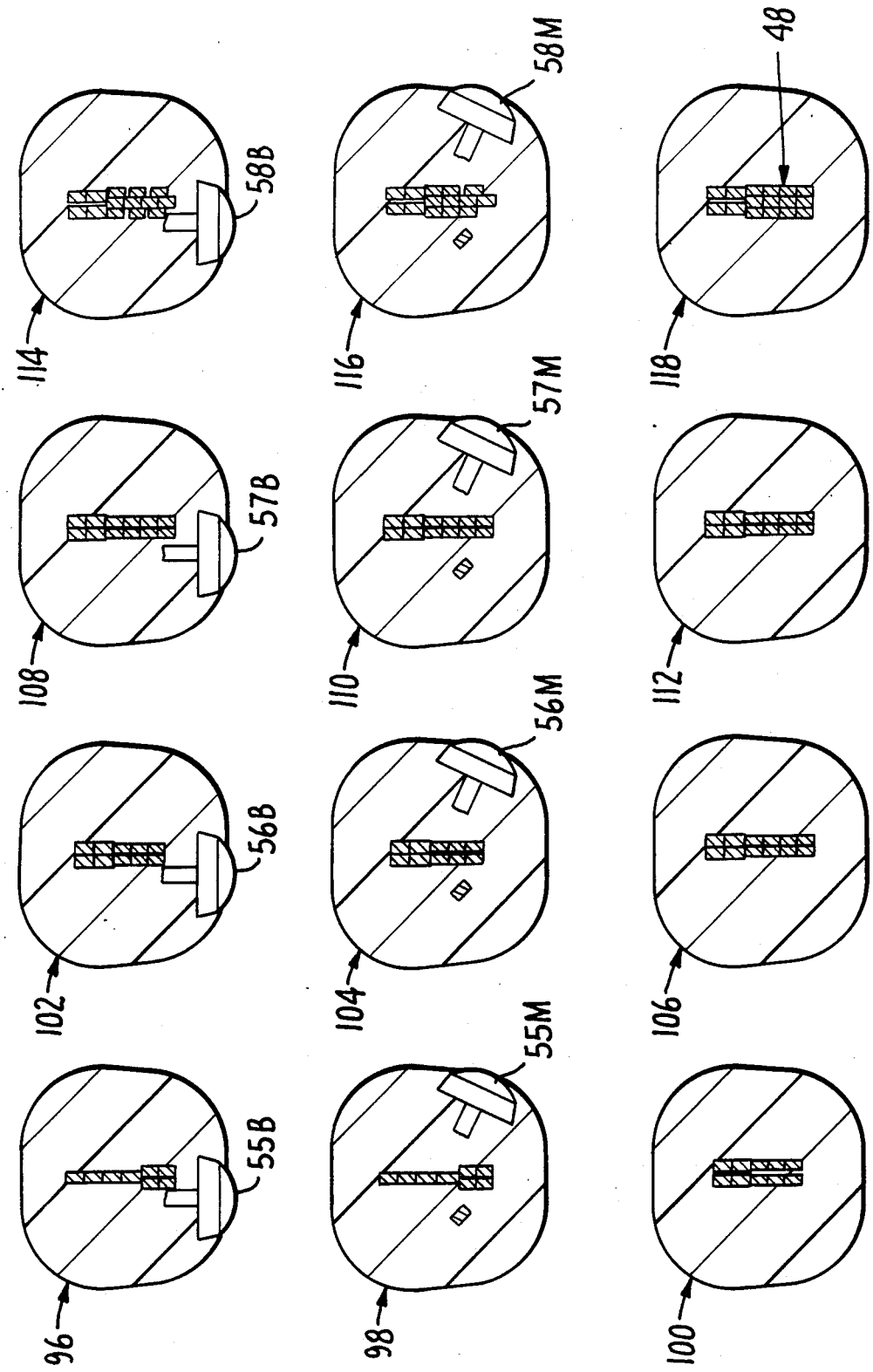

Schematic representations of the cross-section of the FIG. 3 array at various locations are shown in FIGS. 6A and 6B. By way of example, cross-section 72 of FIG. 6A shows basilar electrode 51B (the electrode array is inverted). Cross-section 74 shows modiolar electrode 51M and the insulated lead 120 extending from electrode 51B towards the central portion of the carrier. Insulated lead 120 is seen partially rotated from the horizontal position as it curves away from 51B, into the required vertical position in the central rib. Cross-section 76 is taken between electrodes 51M and 52M. At this position, lead 120 from electrode 51B and another lead from electrode 51M are positioned within the central portion of the carrier to form central rib structure 48.

As further cross-sections are taken through the electrode array towards the basal end of the array, additional electrode leads are added to center rib structure 48. As shown in the FIG. 6B cross-section 118, and in FIG. 6c taken past the last electrode 58M, central rib structure 48 is comprised of sixteen separate electrode leads.

The electrodes and electrode leads are fabricated from noble metals which resist electrolytic corrosion. An alloy containing 90% platinum and 10% iridium has been found to be ideal for the present application. Junctions between dissimilar metals must be avoided. It is preferred that the electrodes and leads form an integral structure. A novel method of fabricating the electrodes and associated leads will now be described. All fabrication takes place in a Class 100 clean room.

The electrodes and leads are fabricated from flattened platinum/iridium wires which are covered with a layer of insulation. The insulation must be non-toxic and non-bioreactive. A polyimide insulation sold under the trademark "Pyre ML" has been found suitable for the present application. Such insulated flattened wires may be obtained from California Fine Wire of Grove City, Calif.

As will subsequently be explained, it is preferred that the electrodes and leads positioned near the apical end of the array be fabricated from a heavier gauge platinum/iridium wire than the remainder of the electrodes and leads. In this regard, electrode pairs 51B, 51M, 52B, and 52M and the associated leads are fabricated from wires having a width of approximately 0.075 mm and a thickness of approximately 0.025 mm (without insulation). Electrode pairs 53B-58M are fabricated from wire having a somewhat smaller cross-section of 0.055 mm by 0.020 mm.

Figures 9A, 9B, 9C:
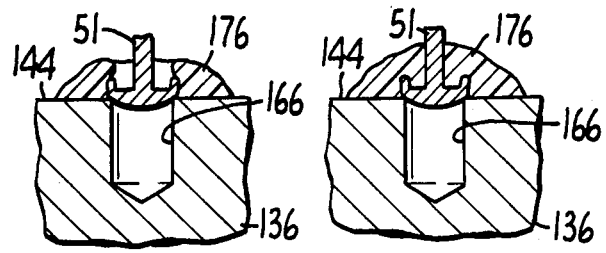
FIGS. 9A through 9E depict the method by which individual electrodes are installed in the lower removable mold member of FIG. 8.
Figures 9D, 9E, 11:
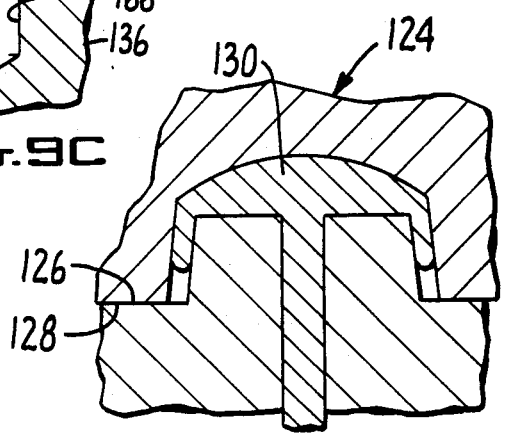
FIG. 11 is a cross-sectional view of the hammer and anvil sections of the swaging tool used to form the individual electrodes of the subject electrode array.

The insulated platinum/iridium wires of the appropriate gauge are cut into sixteen separate sections of approximately 11 cm. Approximately 6 mm of each wire is burned back utilizing a micro acetylene torch to melt the wire to form a sphere approximately 0.28 mm in diameter. The wire is then inserted in an electrode forming swaging tool as depicted in FIG. 11.

The swaging tool, generally designated by the numeral 124, includes a fixed lower steel anvil section 126 and a movable upper steel hammer section 128. Anvil section 126 is provided with a pedestal having a circular cross-section with a diameter of approximately 0.30 mm and a height of approximately 0.11 mm at the top and 0.33 mm at the base (not designated). A rectangular opening is provided in the center of the pedestal for receiving the wire. Separate anvil sections are utilized for the two gauges of wire.

Hammer section 128 is provided with a recess having a circular cross-section, which is approximately 0.20 mm deep in the central portion. The recess includes a central concave section which is approximately 0.35 mm in diameter surrounded by a skirt section which extends from the periphery of the concave section to the bottom of the hammer section where the diameter of the recess is approximately 0.38 mm.

Hammer section 128 is retained in a guiding assembly (not shown) which permits the section to move freely in the vertical direction while maintaining the section centered over the anvil section. In operation, the hammer section is lifted to permit the end of the wire to be inserted in the opening in the anvil section pedestal with the sphere resting on the upper surface of the pedestal. The hammer is then manually lifted a predetermined distance, typically 2 cm, and then released. The force of the hammer striking the sphere causes a general mushroom-shaped electrode 130 to be formed from the sphere.

It is important to maintain a relatively constant surface on each of the electrodes used in the subject electrode array. The FIG. 11 swaging tool will provide a constant covex surface area even though the volume of the sphere formed on the end of the wire may vary. The preferred embodiment electrode is provided with a relatively vertical skirt member which extends around the convex upper surface of the electrode. The skirt member, which does not form part of the final electrode surface, is formed between the side of the pedestal of the anvil section and the parallel skirt section of the hammer and is approximately 0.05 mm thick. The length of the skirt section will vary depending upon the volume of the original sphere, thereby compensating for errors in the sphere diameter so as to maintin a constant electrode surface area. The skirt section of the electrodes are preferably disposed at approximately a 5 degree angle from vertical to facilitate the forming and removal of the electrode and integral lead from the swaging tool.

After the electrodes are formed they are cleansed in alcohol to remove charred insulation and the like. The leads of the electrodes are then coated with a second layer of insulation. An insulation marketed by Union Carbide, Electronics Division of San Diego, Calif., under the trademark Parylene C has been found suitable for this application.

It is believed that performance of the electrodes may be improved by coating the convex surface of the electrodes with a layer of iridium oxide. This may be accomplished in various ways. First, a solution may be prepared by dissolving Iridium chloride in a solution of isopropanol and hydrochloric acid. A single droplet of the solution is deposited on the convex surface of the electrode and then the electrode is placed in a 320° C. oven until the droplet has completely dried and the iridium chloride is converted to iridium oxide. This procedure is repeated three or four times thereby causing a layer of iridium oxide to be formed on the surface of the electrode. Alternatively, an iridium oxide layer may be sputtered directly onto the electrode using an iridium target in an argon and oxygen plasma. Also, the electrode may be sputter-coated or electroplated with pure iridium, and then baked in an oxygenated furnace to oxidize the iridium film.

Once the electrodes have been formed, a sphere is formed on the opposite end of the electrode lead with a final lead length of approximately 75 mm. It will be necessary to add additional platinum/iridium wire to form the desired sphere diameter of approximately 0.5 mm. The spheres at the ends of the electrode leads serve as the electrode contacts of contact pad 30 (FIG. 1A). Once the electrodes and leads have been cleansed in alcohol, they are ready for assembly in the electrode array.

The elastomer carrier which supports the electrodes and associated leads are preferably cast using injection molding techniques. The casting fixture shown in FIG. 7 includes an upper main mold member, generally designated by the numeral 132 and a separate lower main mold member, generally designated by the numeral 134. The upper and lower mold members, which are machined stainless steel, each are provided with a transverse notch (not designated) having an inclined surface 170.

A lower removable intracochlear mold member 136 is positioned within the transverse notch of lower main mold member 134. Member 136 has an inclined surface (not designated) which abuts and slidably engages inclined surface 170 of member 134. A pair of mounting blocks are disposed on opposite sides of mold member 136 in the notch and are spaced apart from the member. Adjustment screws (not designated) extend through threaded openings in block 140 so as to engage mold member 136. The adjustment screws are used to alter the lateral position of member 136 on the lower main mold member 134. A third screw extends through the end of the main mold member 134 and engages mold member 136 so as to force the member against inclined surface 170. A similar arrangement is used to secure an upper intracochlear mold member 138 in a notch machined in upper main mold member 132.

Lower intracochlear member 136 has a spiral-shaped cavity 144 (FIG. 10) which generally corresponds to the intracochlear section of the electrode array of FIG. 3. A corresponding spiral-shaped cavity 142 is machined into the upper intracochlear mold member 138. Mold members 136 and 138 are removable to facilitate the machining of cavities 144 and 142 and other fabrication steps.

An elongated lead cavity 148 is machined down the central portion of lower main mold member 134 which terminates in a contact pad cavity 158. Cavity 158 is used to form contact pad 28 (FIG. 1A). Upper main mold member 132 is machined to provide an elongated upper lead cavity 146 which terminates by gently tapering to the surface at the same distance from 170 that corresponding cavity 148 intersects the edge of cavity 158.

Upper main mold member 132 is provided with four downward projecting alignment studs 154 which are received by corresponding bore 156 machined in the lower main mold member 134. When the alignment studs are positioned within the corresponding bores, the upper and lower lead cavities are in registration. The adjustment screws of blocks 140 are used to alter the position of the two intracochlear mold members 136 and 138 so that the upper and lower spiral cavities 142 and 144 are in registration.

Upper main mold member 132 carries eight screws 150 which are positioned in openings 164. The screws are retained in the openings by set screws 160. The set screws have central openings to provide access to the heads of screws 150. Lower main mold member 134 is provided with eight threaded bores 152 for receiving screws 150.

Although not depicted, an elastomer reservoir is formed in upper main mold member 132. A series of small openings extend from the reservoir into the upper lead cavity 146. In addition, a channel is provided in the surface of upper intracochlear mold member 138 which couples the reservoir to spiral-shaped cavity 142.

Figure 8:
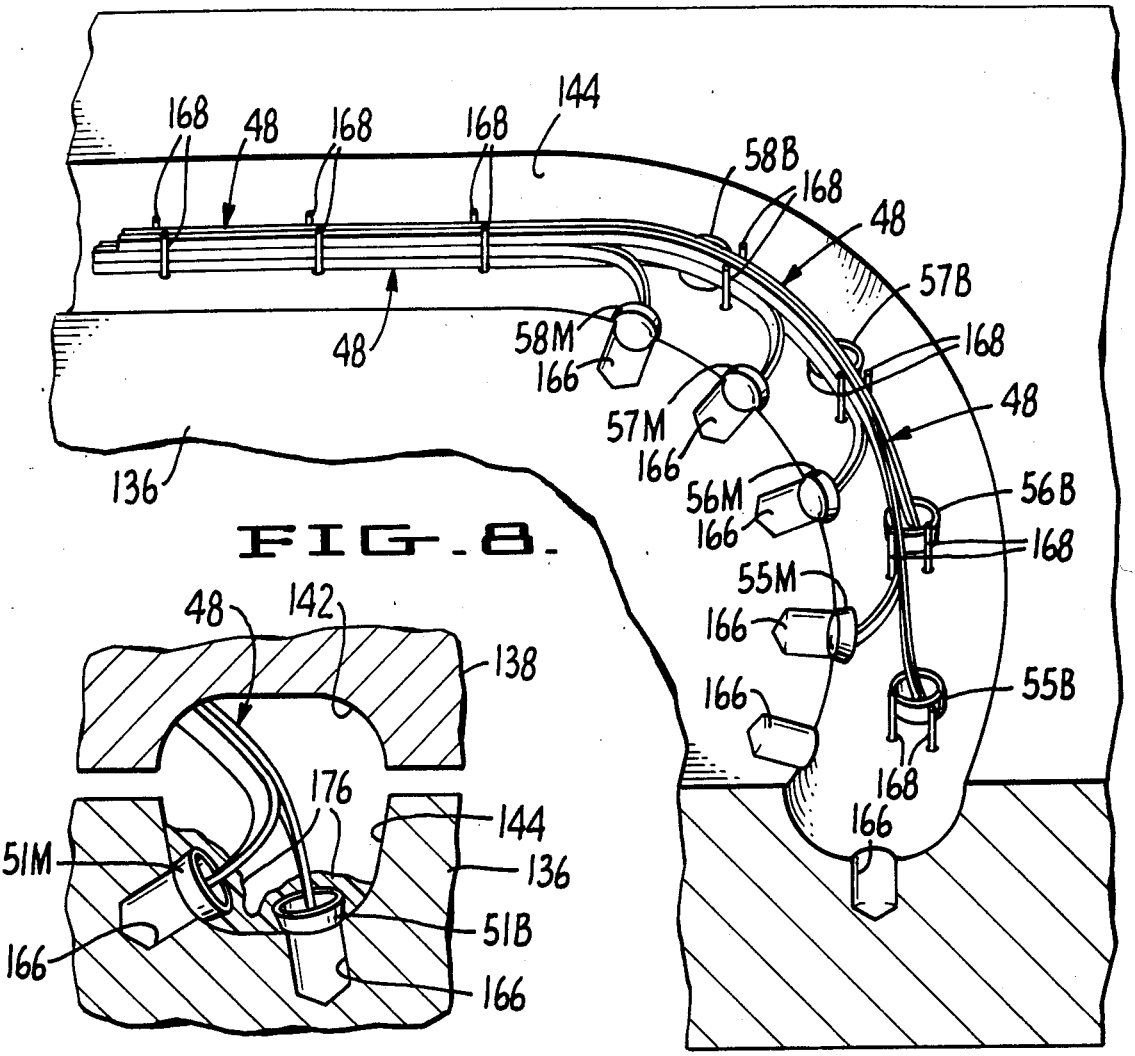
FIG. 8 is a sectional view of the lower removable mold member of the FIG. 7 casting fixture for forming the cochlea section of the subject electrode array.

Prior to the casting of the elastomer, the mold sections are cleansed. Next, the electrodes and associated leads are installed within the lower spiral cavity 144 and lead cavity 148. FIG. 8 is a cross-sectional schematic view of a portion of lower intracochlear mold member 136, with a top section removed. Some of the electrodes and associated leads are shown installed in cavity 144 prior to the casting of the elastomer carrier.

It is necessary to precisely align the various electrode within the mold prior to casting. A series of bores 166 are drilled in cavity 144 at each desired electrode position. The cross-sectional area of bores will be essentially the same as the exposed electrode area, which is preferably 0.1 mm.

An elastomer gasket is formed over each bore 166 to hold the electrodes in place. The sequence for forming the gaskets and securing the electrodes is depicted in FIGS. 9A through 9E. As shown in FIG. 9A, a temporary pin 174 is positioned within each positioning bore 166. Pins 174 have a diameter approximately equal to the bore diameter. Next, a small quantity of uncured elastomer material 176 such as Silastic brand elastomer, is deposited around each pin using a syringe or the like. Mold member 136 is preferably resting on a hot plate which heats the member to approximately 250° F. to 300° F. The heated mold member causes the elastomer to cure within a few seconds.

Once the elastomer has cured, pins 174 are removed as depicted in FIG. 9C. Prior to removal, a short length of metal tubing having an inside diameter slightly larger than that of pins 174 is positioned over the pin with the bottom of the tubing resting against the elastomer material 176. The pins are then extracted through the tubing, with the tubing serving to retain the elastomer material in place around bore 166.

The electrode 51 to be installed is then positioned over the appropriate bore 166 and forced downward causing the electrode to enter the opening formed in the gasket comprising material 176 and become positioned adjacent the periphery of bore 166. Next, an additional small quantity of elastomer is injected over the electrode, thereby securing the electrode in place and sealing the positioning bore 166.

Figure 10:
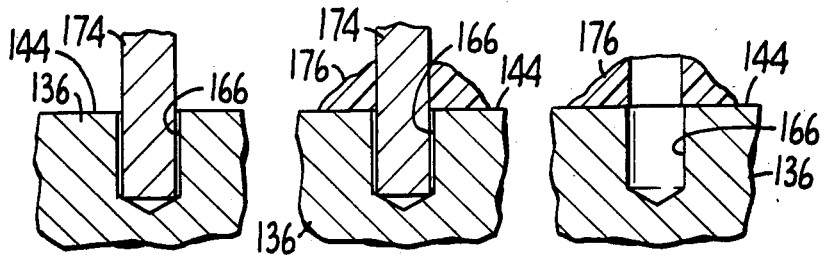
FIG. 10 is a fragmentary cross-sectional view of the upper and lower removable mold member which form the cochlea section of the electrode array prior to the injection of the elastomer.

FIG. 10 is a further cross-sectional view of a portion of intracochlear mold member 136 in the region of electrodes 51M and 51B prior to the casting of the elastomer carrier. The two electrodes are depicted as having the same longitudinal position, although the electrodes are actually longitudinally spaced apart.

The cross-sectional area of the cavity formed between the lower and upper intracochlear mold members 136 and 138 is fixed at one value between the positions for electrodes 51B and 53M and anther larger value between the positions for electrodes 54B and the remainder of the electrodes as indicated by curve 61 of FIG. 4. The taper between the two cross-sections occurs between the positions for electrodes 53M and 54B.

Returning to FIG. 10, for the small cross-sectional area cavity 144 has a center depth of 0.5 mm and cavity 142 has a center depth of 0.25 mm. The average width of the two cavities is 0.75 mm, with the sidewalls of cavity 144 being slightly tapered. The four cross-sectional corners of the cavities have a radius of 0.25 mm. The center axis for the modiolar electrode positioning bores 166 for the small cross-sectional portion is displaced below the horizontal axis by 40° with the distance between the upper most periphery of bores 166 and the top surface of the mold being approximately 0.2 mm so as to provide sufficient area for the elastomer material 176. Bores 166 for the basal electrodes have a vertical central axis which is offset from the center of cavity 144 by 0.10 mm so as to provide clerance for the electrode leads.

For the larger cross-sectional area of array, cavity 144 has a center depth of 0.625 mm and cavity 142 has a center depth of 0.375 mm. The average width of the two cavities is 1.0 mm, and the sidewalls of the cavity are slightly tapered. The four cross-sectional corners of the cavities have a radius of 0.375 mm, and the center axis for the modiolar electrode positioning bores 166 for the large cross-sectional portion is displaced below the horizontal axis by 30°. The distance between the uppermost periphery of bores 166 and the top surface of the mold is again approximately 0.2 mm and the basilar electrode bore is offset from the center of cavity by 0.100 mm.

Prior to the installation of the electrodes over bores 166 in the elastomer gasket, the insulated electrode leads must be positioned generally down the center of cavity 144. A series of guide pins 168, arranged in spaced-apart pairs, are disposed along the length of the lower spiral cavity 144 and the lead cavity 148. The bottom portion of the cavities are provided with openings (not designated) for temporarily receiving the guide pins. In cavity 144, the guide pins are positioned generally intermediate adjacent electrode pairs, or about every 2 mm. The guide pin pairs may be spaced significantly further apart along the generally linear portion of cavity 144 and along cavity 148.

The electrodes and associated leads are first positioned between the guide pin pairs 168 along the linear portion of cavities 144 and 148 with the connector spheres (not shown) being positioned generally over contact pad cavity 158. The relative position of the large and small gauge leads are preferably as shown in FIG. 6C although other lead arrangements may be used. As indicated by cross-section 118 of FIG. 6B, the relative spacing of guide pins 168 in this region should be great enough to snugly receive three horizontally-positioned small-gauge leads, with the individual leads aligned vertically between the guide pins. By way of further example, cross-section 106 of FIG. 6B indicates that the guide pins 168 positioned between electrodes 56M and 57B should be spaced apart to snugly receive two horizontally-positioned large-gauge leads, with the individual lead aligned vertically between the pins.

It is important that all of the electrode leads be individually vertically aligned between the guide pins. Once all of the leads are in position, the individual electrodes are inserted in the elastomer gaskets 144 (FIG. 9D) as previously described. Since the electrode leads are individually vertically aligned, it will be necessary to twist the electrode leads, as depicted in FIG. 10, in order to insert the electrodes into the gaskets.

Once the electrodes have been inserted and secured in place using additional elastomer material, the connector spheres are positioned in the appropriate openings in the contact pad cavity 158. It is important to note that the path taken by each electrode lead for a given contact pad cavity opening to the associated positioning bore 166 is constant, therefore the electrode leads may be of a single length and interchangeable (except for the large and small gauge leads) thereby greatly simplifying assembly of the array.

Once the electrodes have been tacked in position with a quantity of elastomer, small quantities of elastomer are deposited at various points along the electrode lead path to secure the leads together and to the surface of the mold cavity. Next, the guide pins 168 are removed from their respective bores. The assembly is now ready for injecting the uncured elastomer so as to form the carrier.

The carrier may be cast either using injection molding, centrifugal molding or a combination of both. First the upper main mold member 132 is installed on the lower main mold member 134. The two members are secured together by tightening screws 150. Next, a suitable quantity of elastomer is mixed with the appropriate catalyst and centrifuged in a vacuum environment to remove any air bubbles. The elastomer is then added to the reservoir of the casting fixture. The fixture is then installed on a centrifuge utilizing mounting bore 162 and returned to a vacuum environment. The fixture is then centrifuged for approximately fifteen minutes at three G's so as to propel the uncured elastomer from the reservoir through the numerous small openings into the mold cavity.

After centrifuging, the fixture is removed from the vacuum environment and placed in a curing oven or hotplate set at approximately 200° F. for several hours. Once the elastomer is cured, screws 150 are unscrewed causing the upper main mold member 132 to separate from the lower member 134. The formed electrode array is then carefully removed from the lower mold member and the flash is removed using nippers.

The elastomer carrier is elastic and retains a memory of the original shape of the mold. The grouped electrode leads which form the central rib structure 48 have some tendency to straighten the intracochlear portion of the array so as to cause the array depicted in FIG. 3 to uncurl approximately one-quarter turn.

The surgical handling properties of the intracochlear portion of the electrode array are governed by the central rib structure and the elasticity of the carrier. There tends to be a sharp decrease in the stiffness of a conventional central rib structure at the position of each electrode pair when flexed from the basal portion of the array and moving toward the tip of the array, since there are progressively fewer electrode leads present in the rib structure. However, by utilizing a relatively large gauge wire or otherwise stiffer wire in the leads extending into the apical portion of the array, the flexibility of the array becomes more uniform.

The apical tip of conventional electrode arrays also had a tendency to curl upward and out of the plane of the cochlear spiral during the implantation procedure, so as to cause damage to the basilar membrane. The disclosed central rib structure 48 greatly reduces the tendency of the tip to deflect out of the plane of the cochlear spiral, but provides an anisotropic and longitudinally consistent stiffness which permits the array to flex smoothly in the plane. This is achieved by virtue of the use of electrode leads having an elongated cross-section which are individually aligned vertically, i.e., the major axis of the cross-section is transverse to the plane of the spiral.

In addition, the relative placement of the electrode leads in the central rib structure contributes to the desired physical properties of the array. It is preferred that the leads be stacked in a vertical arrangement with respect to the spiral plane, as opposed to a horizontal arrangement, to the extent possible. This further enhances the stiffness of central rib structure 48 in the vertical direction yet allows for the desired flexing in the horizontal plane. Given the height restrictions of the scala tympani, and therefore the maximum thickness of the electrode array, it is not possible to stack all of the lead vertically throughout the length of the electrode array as shown in cross-section 82 of FIG. 6A. For example, at cross-section 94 of FIG. 6A, it is necessary to position some of the leads horizontally so as to limit the height of central rib structure 48. Similarly, FIG. 6C shows a preferred lead stacking arrangement in the area of the array where central rib structure 48 includes all sixteen leads, such as in the region between the basal end of the array and electrode 58M. Other suitable lead stacking arrangements can be used to achieve the desired results.

It is generally desirable to maximize the exposed surface area of the individual electrodes so as to reduce the current densities and thereby to minimize the possibility of tissue damage and the like. The preferred exposed electrode area may range from approximately 0.08 mm$^2$ to approximately 0.12 mm$^2$ with the preferred approximate area being 0.1 mm$^2$ as previously noted.

In view of current spread between electrode pairs which tends to cause channel interaction, approximately 2.0 mm has been found to be ideal electrode pair spacing for patients with good auditory nerve survival in the basilar membrane, although spacing of approximately 1.6 mm would be adequate and provide meaningful channel resolution. This measurement is made from the center of one basilar electrode to the center of the adjacent basilar electrode. For patients having poor nerve survival, the pair spacing should be increased from 2.0 mm to enable the patient to resolve the individual channels. The objective for most patients is to space the electrode pairs a sufficient distance so as to achieve channel resolution, yet not too great a distance so as to be unable to stimulate a portion of surviving nerves between the electrode pairs. It has been found that the maximum pair spacing for such patients is approximately 2.4 mm.

In order to more effectively stimulate the auditory nerves in the basilar membrane, it has been found that the modiolar electrode should be positioned as near to the basilar membrane as possible without causing severe current shunting between the electrodes. The angle of inclination of the modiolar electrode should be displaced above the plane of the electrode array spiral by at least 20° and not more than 50°.

The center-to-center spacing of the basilar and modiolar electrodes within a pair should be at least 0.650 mm, measured from center to center, with a spacing of 0.800 mm being found to be optimal, and 1.00 mm being the maximum value. The longitudinal offset of the electrodes within a pair should be approximate 0.20 mm to 0.60 mm, with 0.40 being found to be optimum.

It is important that the intracochlear portion of the electrode array rest within the scala tympani in a relaxed condition without exerting force against any structures within the scala tympani. Therefore, the intracochlear portion of the array must have a spiral form which matches the spiral of the cochlea and which generally correspondes to the following equation:

$$R = 5.4e^{-0.16\phi} \quad (1)$$

Where R is the radius of the spiral in milimeters and $\phi$ is the angle in radians.

As previously noted, the intracochlear portion of the subject electrode array includes a basal portion and an apical portion having differing cross-sectional dimensions. It has been found for most patients that the basal portion should not have a height which exceeds approximately 1 mm (measured vertically with respect to the spiral plane) and should not exceed approximately 18 mm in length. Further it has been found that the apical portion should not have a height which exceeds approximately 0.80 mm and should preferably not extend beyond 8 mm from the basal portion of the array.

The electrode leads associated with the electrodes positioned in the apical portion of the array should be relatively stiffer than the remaining electrode leads. At least the most apical three electrode pairs, and preferably only the most apical two pairs should have relatively stiff leads in comparison to the remaining leads.

Thus a novel electrode array and method of manufacturing same has been disclosed. Although preferred embodiments of the subject array and method have been described in some detail, it is to be understood that various changes can be made by persons skilled in that art without departing from the spirit and scope of the invention as defined by the appended claims.

We claim:

1. A method for making an intracochlear multielectrode array, having an apical portion and a basal portion and a spiral shape at least generally conforming to the scala tympani of a cochlea, said array comprising an elastomeric carrier having a plurality of metallic electrodes, each having an associated lead to form a plurality of leads extending from the basal portion into the apical portion of said array, supported in fixed positions by said carrier, said method comprising the steps of fabricating each elctrode and associated lead from a flattened metallic wire by forming said electrode on a first end of said wire to have a covex outer surface.

2. The method of claim 1 wherein said fabricating step further comprises forming a an electrical connector contact on a second end of said wire.

3. The method of claim 2 wherein said last mentioned forming step comprises forming said contact into a sphere.

4. The method of claim 1 further comprising covering said wire with an adherent layer of non-toxic and non-bioreactive electrical insulation prior to said fabricating step.

5. The method of claim 4 further comprising melting the first end of said wire to form a spherical electrical contact.

6. The method of claim 4 further comprising coating said lead with a second layer of insulation after said fabricating step.

7. The method of claim 1 further comprising coating the convex outer surface of said electrode with iridum oxide.

8. The method of claim 1 wherein said fabricating step comprises fabricating leads extending from the basal portion into the apical portion of said array from wires having a heavier gauge than other ones of said leads terminating short of the apical portion of said array to form a rib structure for said array that flexes substantially uniformly throughout the length thereof.

9. The method of claim 1 wherein said fabricating step further comprises forming a skirt member around the convex outer surface of said electrode.

10. A method of maufacturing an electrode array for implanting in a human cochliea comprising the following steps:
providing a plurality of electrodes, each having an associated electrode lead;
disposing said plurality of electrodes and associated leads in a mold cavity defined in a mold to position said electrodes at predetemined spaced positions relative to each other to effectively stimulate auditiory nerves when said array is implanted in a human cochlea and to form said leads into a rib structure for said array,
securing said electrodes at said predetermined spaced positions in the cavity of said mold utilizing an elastomer material; and
after securing said electrodes, casting a resilient carrier within said cavity in encapsulating relationship about said leads to form a rib structure for said array and to position and secure said electrodes at said predetermined positions and to expose outer surface portions thereof on said array.

11. A method for making an intracochlear multielectrode array, having an apical portion and a basal portion and a spiral shape at least generally conforming to the scala lympani of a cochlea, said array comprising an elastomeric carrler havlng a plurality of metallic electrodes, each having an associated lead to form a plurality of leads extending from the basal portion into the apical portion of said array, supported in fixed positions on said carrier to expose an outer surface of each said electrode on said array, said method comprising the steps of
fabricating each of said electrodes and associated leads,
placing said electrodes and associated leads in first cavities, defined in a first mold member, conforming to the shape of said array.
positioning said leads to form a central rib structure for said array that is flexible to permit uncurling of said rib structure, but is relative inflexible in a direction transverse to the direction of such uncurling,
securing a second mold member, having second cavities at least generally conforming to said first cavities, to said first mold member to superimpose said first and second cavities which jointly conform to the shape of said array,
filling said first and second cavities with an uncured elastomer, and
curing said elastomer to form said carrier and said array.

12. The method of claim 11 wherein said fabricating step comprises forming each said electrode on a first end of a wire and further comprising forming an electrical connector contact on a second end of said wire with said wire thus connected directly between said electrode and said contact, placing said contact in a contact pad cavity defined in said first mold member, filling said contact pad cavity with said uncured elastomer, and curing the elastomer in said contact pad cavity to form a contact pad connected to said array by said associated wire.

13. The method of claim 11 wherein said first and second cavities define a spiral-shaped cavity, conforing to the spiral shape of said array, and a plurality of bores, each having a cross-sectional areas essentially the same as that of the exposed outer surface of a respective electrode, formed in spaced apart relationship relative to each other in wall portions defining said spiral-shaped cavity, and wherein said placing step comprises positioning the exposed outer surface of each said electrode in a respective one of said bores.

14. The method of claim 12 further comprising forming an elastomeric gasket adjacent to each said bore and holding a said electrode at said bore by said gasket, prior to said filling step.

15. The method of claim 14 further comprising fixing said electrode in position and simultaneously sealing said bore by applying a small quantity of elastomer over said electrode and gasket, prior to said filling step.

16. The method of claim 12 wherein said fabricating step comprises forming a skirt member around the outer surface of said electrode and said fixing step comprises encapsulating said skirt member with said small quantity of elastomer.

17. The method of claim 15 further comprising arranging a plurality of removable pins in said first cavities to define a pathway for said leads, positioning said leads in said pathway between said pins to form said rib structure, and removing said pins, subseuent to said applying step and prior to said securing step.

18. A method for making an intracochlear multielectrode array, having an apical portion an a basal portion and a spiral shape at least generally conforming to the scala tympani of a cochlea, said array comprsiing an elastomeric carrier having a plurality of metallic electrodes, each having an associated lead to form a plurality of leads extending from the basal portion into the apical portion of said array, supported in fixed positions on said carrier to expose an outer surface of said electrode on said method comprising the steps of
fabricating each electrode and associated lead from a flattened metallic wire, including fabricating a first group of said leads from wires having a heavier gauge than a second group of said leads,
placing said electrodes and associated leads in a mold defining cavities conforming to the shape of said array, including extending only said first group of leads into an apical end of said cavities to form a central rib structure for said array that flexes substantially uniformly throughout the length thereof,
filling said cavities with an uncured elastomer, and
curing said elastomer to form said carrier and said array.

19. A method for making an intracochlear multielectrode array, having an apical portion and a basal portion and a spiral shape at least generally conforming to the scala tympani of a cochlea, said array comprising an elastomeric carrier having a plurality of metallic electrodes, each having an associated lead to form a plurality of leads extending from the basal portion into the apical portion of said array, supported in fixed positions on said carrier to expose an outer surface of each of said elctrodes on said array, said method comprising the steps of fabricating each of said electrodes and associated lead from a flattened wire of rectangular cross-section having a width substantially large than its thickness, placing said electrodes and associated leads in a mold defining cavities conforming to the shape of said array, including stacking substantial portions of at least some of said leads in stacked alignment relative to each other to form a rib structure in said array flexible in a horizontal plane containing the full spiral shape of said array, but relatively inflexible in a vertical plane perpendicular to said horizontal plane, filling said cavities with an uncured elastomer, and curing said elastomer to form said carrier and said array.

* * * * *

UNITED STATES PATENT AND TRADEMARK OFFICE
CERTIFICATE OF CORRECTION

PATENT NO. : 4,686,765

DATED : August 18, 1987

INVENTOR(S) : CHARLES L. BYERS, ET AL.

It is certified that error appears in the above-identified patent and that said Letters Patent is hereby corrected as shown below:

Col. 1, line 58, change "embod,iment" to --embodiment--.

Col. 12, line 5, change "correspondes" to --corresponds--.

Col. 12, line 51, delete "a".

Col. 13, line 12, change "cochliea" to --cochlea--.

Col. 13, line 35, change "lympani" to --tympani--.

Col. 13, line 36, change "carrler havlng" to --carrier having--.

Col. 14, line 6, change "conforing" to --conforming--.

Col. 14, line 8, change "areas" to --are--.

Col. 14, line 15, change "12" to --13--.

Col. 14, line 23, change "12" to --15--.

Col. 14, line 32, change "subse-uent" to --subsequent--.

Col. 14, line 35, change "an" to --and--.

Col. 14, line 37, change "comprsiing" to --comprising--.

Col. 14, line 44, after "said" insert --array, said---.

UNITED STATES PATENT AND TRADEMARK OFFICE
CERTIFICATE OF CORRECTION

PATENT NO. : 4,686,765

DATED : August 18, 1987

INVENTOR(S) : CHARLES L. BYERS, ET AL.

It is certified that error appears in the above-identified patent and that said Letters Patent is hereby corrected as shown below:

Col. 15, line 3, change "large" to -- larger --.

Signed and Sealed this

First Day of March, 1988

Attest:

DONALD J. QUIGG

Attesting Officer

Commissioner of Patents and Trademarks